United States Patent [19]

Flagg et al.

[11] 4,224,898
[45] Sep. 30, 1980

[54] METHOD AND MEANS FOR ANESTHETIZING INSECTS

[75] Inventors: Raymond O. Flagg; Richard L. Franks, both of Burlington, N.C.

[73] Assignee: Carolina Biological Supply Company, Burlington, N.C.

[21] Appl. No.: 42,246

[22] Filed: May 24, 1979

[51] Int. Cl.³ ............................................. A01K 67/00
[52] U.S. Cl. .......................................... 119/1; 119/15
[58] Field of Search ................... 119/1, 15; 128/204.13

[56] References Cited

U.S. PATENT DOCUMENTS

| | | | |
|---|---|---|---|
| 3,769,936 | 11/1973 | Swanson et al. | 119/1 |
| 3,871,330 | 3/1975 | Swanson et al. | 119/1 |
| 4,106,438 | 8/1978 | Nelson | 119/1 |

*Primary Examiner*—Hugh R. Chamblee
*Attorney, Agent, or Firm*—Bell, Seltzer, Park & Gibson

[57] ABSTRACT

Insects, such as fruit flies, are quickly anesthetized while contained in a culture vessel of the type having a mouth closed by a flexible porous plug by immersing one end portion of an elongate slender applicator wand in a volatile liquid anesthetic and then inserting the applicator wand between the wall of the culture vessel and the porous plug without removal of the plug and without creating an opening therebetween to allow the insects to escape and positioning the end portion of the applicator wand inside the culture vessel to thereby quickly expose the insects in the culture vessel to the anesthetic.

9 Claims, 6 Drawing Figures

U.S. Patent    Sep. 30, 1980    4,224,898
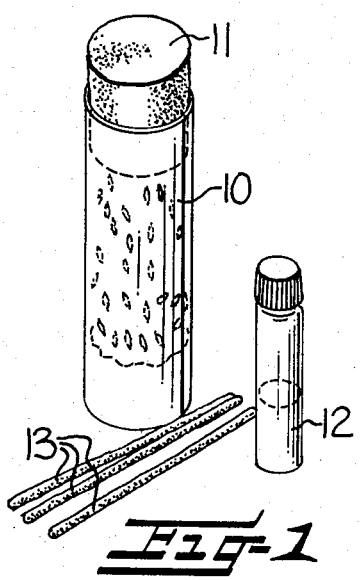
Fig-1
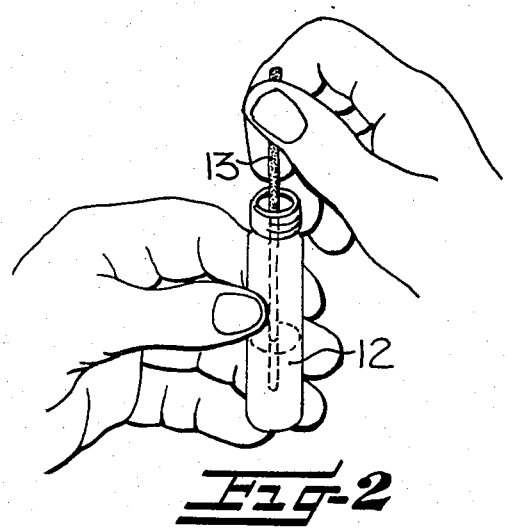
Fig-2
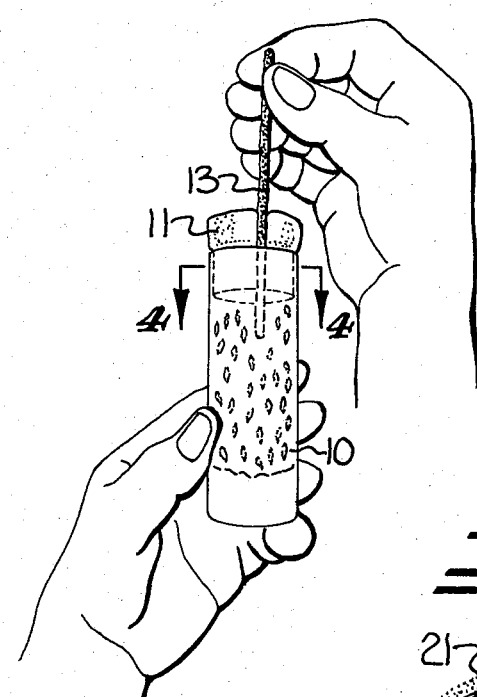
Fig-3
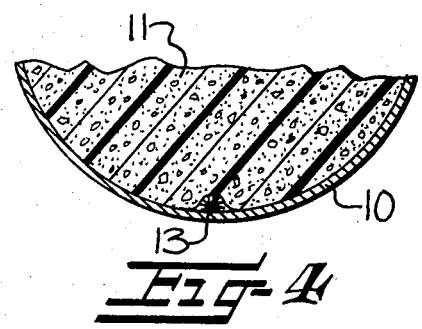
Fig-4
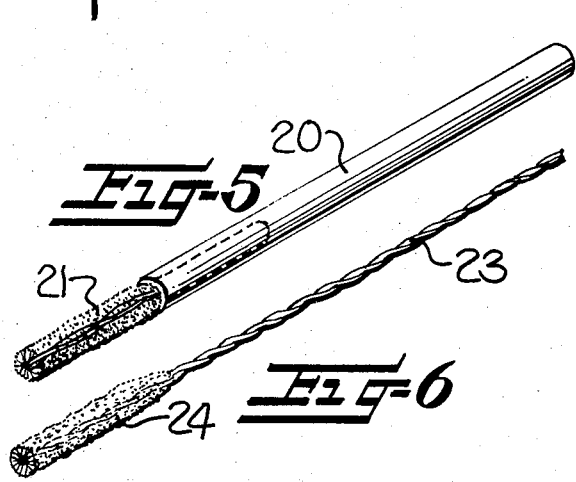
Fig-5
Fig-6

METHOD AND MEANS FOR ANESTHETIZING INSECTS

FIELD OF THE INVENTION

This invention relates to the anesthetizing of insects, and in particular to a method and means for anesthetizing insects such as fruit flies while contained in a culture vessel.

BACKGROUND OF THE INVENTION AND PRIOR ART

In raising or culturing insects such as fruit flies (Drosophila) for genetic studies and the like, the flies are placed in a culture vessel where eggs are laid and the new flies develop to the adult stage. The flies are then anesthetized in order to permit selection and separation of the flies for study and/or further culturing.

The usual practice in anesthetizing involves transferring the flies from the culture vessel to a separate anesthetizing vessel. The flies frequently escape during the transfer, presenting a nuisance in the building, and more seriously, presenting the possibility of contaminating other cultures that must be opened for transfer.

Because of these problems, methods have been proposed for anesthetizing fruit flies within a culture vessel to thereby avoid the necessity of transfer. These methods are carried out without removing the porous plug or cover of the culture vessel by passing the anesthetic as a gas through the porous plug. One proposed method requires placing the entire culture vessel in another chamber into which an anesthetic gas, such as ether, is introduced. The gas then diffuses through the porous plug and into the culture vessel. Another method, disclosed in U.S. Pat. No. 4,106,438, involves placing the mouth of the culture vessel against a nozzle which is connected to a source of anesthetic gas and causing the gas to pass through the porous plug and into the culture vessel. Still another method which has been proposed involves pouring liquid anesthetic directly onto the porous plug or closure and allowing the anesthetic to vaporize and diffuse through the plug and into the culture vessel.

All of these previously proposed methods of anesthetizing insects within a culture vessel suffer the disadvantage of being relatively slow since the anesthetic must pass through the porous plug before it comes into contact with the insects inside the culture vessel. Also, these methods are not well suited for providing accurate control over the amount of anesthetic applied. Additionally, the specialized equipment required by some of these methods, such as pressurized cylinders of anesthetic gas or special chambers, is relatively expensive and not always readily available.

SUMMARY OF THE INVENTION

In contrast to the above-noted prior methods of anesthetizing insects within a culture vessel where the anesthetic gas must pass through the porous plug of the culture vessel, the present invention provides for placing the anesthetic source directly inside the culture vessel without removing the plug.

In accordance with the present invention, a volatile liquid anesthetic is applied to a relatively small applicator and the applicator is then positioned directly inside the culture vessel by inserting the applicator between the wall of the culture vessel and the porous plug without removal of the plug. The anesthetic contained on the applicator vaporizes to thereby quickly expose the insects in the culture vessel to the anesthetic.

Preferably, the applicator is in the form of an elongate wand and the anesthetic is applied thereto by immersing one end portion of the wand in the liquid anesthetic. The elongate wand is of sufficiently small diameter for being inserted between the wall of the culture vessel and the flexible porous plug without creating an opening between the wall and the plug to allow insects to escape.

The invention is particularly suited for providing a metered dosage of the anesthetic so that the insects may be anesthetized as quickly or slowly as desired without adverse effects on the insects. The metered dosage is determined by the extent of immersion of the applicator wand in the anesthetic.

In accordance with one embodiment of the invention the wand is formed of a material which is absorbent throughout its length and the wand is immersed to a predetermined desired depth in the liquid anesthetic to thereby provide a predetermined limited amount of anesthetic on the wand.

In accordance with another form of the invention, the end portion of the wand is absorbent only in a predetermined desired area for abosrbing only a predetermined limited amount of the anesthetic when immersed in the liquid anesthetic.

It will thus be seen that the present invention is much simpler than the previously known methods for anesthetizing insects and has the further advantage of not requiring any expensive or specialized equipment. Additionally, the control over the amount of anesthetic introduced into the culture vessel pursuant to the present invention is far superior to that obtainable by the previously known methods of anesthetizing.

BRIEF DESCRIPTION OF THE DRAWINGS

FIG. 1 is a perspective view showing a culture vessel, together with a vial of liquid anesthetic and several applicator wands for use in carrying out the method of the present invention;

FIG. 2 is a view showing how an end portion of the applicator wand is immersed in the liquid anesthetic pursuant to the invention;

FIG. 3 is a view illustrating how the applicator wand is inserted between the wall of the culture vessel and the flexible porous plug;

FIG. 4 is a cross-sectional view taken substantially along the line 4—4 of FIG. 3 and showing how the applicator wand is positioned between the plug and the wall of the culture vessel without creating an opening to allow insects to escape; and FIGS. 5 and 6 are perspective views showing alternative embodiments for the applicator wand.

DESCRIPTION OF ILLUSTRATIVE EMBODIMENT

Referring now more particularly to the drawings, there is shown in FIG. 1 a culture vessel or vial 10 of the type typically used in the study and culturing of insects such as fruit flies. As illustrated, the culture vessel 10 is of a cylindrical shape and the mouth thereof is closed by a cylindrical porous plug 11 formed of a flexible foam material.

In accordance with the present invention there is provided a supply of a volatile liquid anesthetic in a suitable container such as a small screw-cap vial 12.

Any conventional liquid anesthetic which will vaporize at ordinary room temperature and pressure may be suitably employed, such as ether for example.

Pursuant to the present invention, a relatively small amount of the volatile anesthetic is placed directly inside the culture vessel where it vaporizes to thus quickly anesthetize the insects. This is accomplished by applying the anesthetic to a relatively small adsorbent or absorbent applicator, and then positioning the applicator inside the vessel by inserting the applicator between the plug and the wall of the culture vessel without removal of the plug and without creating an opening between the plug and the wall of the vessel to allow the insects to escape.

In the preferred embodiments of the invention illustrated herein, the applicator is in the form of an elongate slender wand. The wand is of relatively small diameter, e.g. on the order of $\frac{1}{8}$ inch or smaller, and is sufficiently rigid to enable pushing the wand endwise into the culture vessel between the porous plug 11 and the wall of the vessel. The smaller diameter of the wand and the flexible nature of the porous plug 11 permit the wand to be so inserted without creating an opening between the plug and the wall of the vessel of such size as to allow the insects to escape.

In the embodiment of the invention illustrated in FIGS. 1 to 4, the applicator wand, indicated by the reference character 13, is formed of an absorbent material throughout its entire length. A coventional pipe cleaner about three to four inches in length has been found to be particularly well suited for use as an applicator wand in accordance with this embodiment of the present invention. The wire core of the pipe cleaner is quite small in diameter and provides sufficient rigidity for insertion into the culture vessel. The fibrous covering of the pipe cleaner is an effective absorbent medium for the anesthetic, and its flexible resilient nature cooperates with the flexible plug to assist in preventing the formation of any escape openings for the insects.

In carrying out the method of the present invention, the wand 13 is grasped adjacent one end thereof and the opposite end portion of the wand is immersed in the liquid anesthetic to a predetermined depth in the manner illustrated in FIG. 2. The depth of immersion of the wand is determined by the strength of the anesthetic used and the size of the dose of anesthetic which is desired. Typically, the end portion of the wand would be immersed to a depth of from about one-quarter of an inch to about three-fourths of an inch.

The anesthetic-containing end portion of the wand 13 is then positioned between the wall of the culture vessel 10 and the plug 11 and the wand is pushed endwise into the culture vessel until the anesthetic-containing end portion passes beyond the lower end of the plug 11 and enters the interior portion of the culture vessel. The volatile anesthetic contained on the end portion of the wand will vaporize under ordinary conditions of room temperature and pressure to thus quickly expose the insects in the vessel to the anesthetic.

It is contemplated that the items for use in carrying out the method of the present invention may be conveniently marketed in kit form for use with culture vessels of the type illustrated, with the kit including a vial of the liquid anesthetic, a supply of wands, and instructions for use, including the recommended depths of immersion for obtaining various predetermined desired doses of the anesthetic.

FIG. 5 illustrates an alternate form or embodiment for the applicator wand. In accordance with this embodiment of the invention the wand comprises a slender elongate hollow tubular member 20 of a nonabsorbent material such as plastic, with an absorbent wick 21 positioned in the hollow interior thereof and extending from one end of the hollow tubular member 20. The wick 21 is formed of a suitable absorbent material such as a conventional pipe cleaner. The wick 21 extends from the end of the tubular member for a predetermined length and is thus adapted to absorb a predetermined desired amount of anesthetic when immersed in the anesthetic.

The wick 21 may be fixedly secured to the hollow member with a predetermined desired length extending therefrom. Alternatively, the wick may be slideably positionable in the hollow tubular member so that the user can readily adjust the length of the exposed absorbent area of the wick 21 in accordance with the desired dosage to be applied. In either event it will be seen that regardless of the depth to which the end portion of the wand is immersed, only a predetermined limited amount of the anesthetic will be absorbed by the wand, thus avoiding the possibility of an excessive dose of anesthetic being inadvertently administered to the insects.

FIG. 6 illustrates still another form or embodiment for the applicator wand. In accordance with this form of the invention the wand comprises an elongate flexible wire element 23 having an absorbent fibrous covering 24 of predetermined length at one end thereof adapted to absorb a predetermined desired amount of anesthetic when immersed in the anesthetic. The wand of this embodiment is quite similar in construction to a conventional pipe cleaner, but with the fibrous covering located only in a predetermined area at one end of the wire core to form an absorbent area and with the fibrous covering being omitted over the remaining portion of the wire core to serve as a handle.

It will thus be seen that the present invention has provided a simple and inexpensive means and method for quickly anesthetizing insects while the insects are contained in a culture vessel. The invention avoids the necessity of any expensive or specialized equipment and provides for effective control over the size of the dose of anesthetic which is administered.

In the drawings and specification, there have been set forth preferred embodiments of the invention, and although specific terms are employed, they are used in a generic and descriptive sense only and not for purposes of limitation.

What is claimed is:

1. A method for anesthetizing insects, such as fruit flies, while the insects are contained in a culture vessel having a mouth closed by a flexible porous plug, said method being characterized by avoiding the necessity of removing the plug or transferring the insects to another vessel, and said method comprising applying a volatile liquid anesthetic to an applicator, inserting the anesthetic-containing applicator between the wall of the culture vessel and the porous plug without removal of the plug and without creating an opening therebetween to allow the insects to escape, and positioning the anesthetic-containing applicator inside the culture vessel and maintaining the applicator in the culture vessel while allowing the anesthetic to vaporize to thereby expose the insects in the culture vessel to the anesthetic.

2. The method as set forth in claim 1 wherein the applicator comprises an absorbent member and the step of applying a volatile liquid anesthetic to the applicator comprises immersing the absorbent member to a predetermined extent in the liquid anesthetic to thereby obtain a predetermined limited amount of anesthetic on the applicator.

3. The method as set forth in claim 1 wherein the applicator is in the form of an elongate slender wand and the step of applying a volatile liquid anesthetic comprises grasping the elongate wand and immersing one end portion thereof in the liquid anesthetic.

4. A method for anesthetizing insects, such as fruit flies, with a predetermined amount of anesthetic while the insects are contained in a culture vessel having a mouth closed by a flexible porous plug, said method being characterized by avoiding the necessity of removing the plug or transferring the insects to another vessel, and said method comprising immersing an end portion of an elongate slender applicator wand to a predetermined depth in a volatile liquid anesthetic so as to obtain a predetermined desired amount of anesthetic on the wand, inserting the applicator wand between the wall of the culture vessel and the porous plug without removal of the plug and without creating an opening therebetween to allow the insects to escape, and pushing the applicator wand endwise until the anesthetic-containing end portion is positioned inside the culture vessel to thereby expose the insects therein to the anesthetic.

5. Means for anesthetizing insects, such as fruit flies, comprising a culture vessel having a mouth and a flexible porous plug positioned in the mouth for retaining insects in the culture vessel, an elongate slender absorbent wand of a sufficiently small diameter for being inserted between the wall of the culture vessel and the flexible porous plug without creating an opening therebetween to allow insects to escape, and a supply of volatile liquid anesthetic in which the end portion of the absorbent wand may be immersed and thereafter inserted into the vessel to thereby expose the insects to the anesthetic.

6. The invention as set forth in claim 5 wherein said wand is formed of an absorbent material throughout its length and the wand is adapted to be immersed to a predetermined depth in the liquid anesthetic to provide a predetermined desired amount of anesthetic on the wand.

7. The invention as set forth in claim 5 wherein said wand has an absorbent wick of predetermined length located at one end thereof adapted upon being immersed in the anesthetic for absorbing only a predetermined limited amount of the anesthetic.

8. The invention as set forth in claim 7 wherein said wand comprises an elongate hollow tubular member and said absorbent wick is positioned in the hollow member and extends outwardly from one end thereof for a predetermined length.

9. The invention as set forth in claim 7 wherein said wand comprises an elongate flexible wire element having an absorbent fibrous covering of predetermined length at one end thereof adapted upon being immersed in the anesthetic for absorbing only a predetermined limited amount of the anesthetic.

* * * * *